United States Patent [19]

Ramachandran

[11] Patent Number: 4,540,793

[45] Date of Patent: Sep. 10, 1985

[54] SUBSTITUTED PYRIDINES

[75] Inventor: Venkataraman Ramachandran, Baton Rouge, La.

[73] Assignee: Ethyl Corporation, Richmond, Va.

[21] Appl. No.: 532,700

[22] Filed: Sep. 16, 1983

[51] Int. Cl.$^3$ ............................................. C07D 213/26
[52] U.S. Cl. ..................................................... 546/346
[58] Field of Search ................................. 546/345, 346

[56] References Cited

U.S. PATENT DOCUMENTS 3,180,872  4/1965  Cochran, Jr. et al. ............... 546/346
3,804,840  4/1974  Bowden et al. ...................... 546/345

Primary Examiner—Joseph Paul Brust
Attorney, Agent, or Firm—Donald L. Johnson; John F. Sieberth; Patricia J. Hogan

[57] ABSTRACT

4-(1-Chlorovinyl)pyridines are prepared by heating an acid salt of 4-(1,2-dichloroethyl)pyridine in an inert solvent until dehydrohalogenation is effected.

5 Claims, No Drawings

SUBSTITUTED PYRIDINES

FIELD OF THE INVENTION

This invention relates to 4-(1-chlorovinyl)pyridines and more particularly to a process for preparing them.

BACKGROUND

U.S. Pat. No. 3,180,872 (Cochran et al.) generically discloses 2- and 4-(1-halovinyl)pyridines, their acid addition salts, and their utility as nematocides, as well as specifically teaching various 2-vinylpyridine derivatives and one 4-vinylpyridine derivative—4-(1-chlorovinyl)pyridine hydrochloride.

According to column 4, lines 41–55, such compounds can be prepared by converting 2- or 4-vinylpyridine to the appropriate 2- or 4-(1,2-dihaloethyl)pyridine and refluxing that product in anhydrous ethanol. This process appears to have been successfully employed in the preparation of 2-vinylpyridine derivatives but has been found to be unsatisfactory in the preparation of 4-(1-chlorovinyl)pyridine derivatives because of the reactivity of ethanol toward 4-(1,2-dichloroethyl)pyridine. For example, an attempt at preparing 4-(1-chlorovinyl)pyridine by refluxing 4-(1,2-dichloroethyl)pyridine hydrochloride in ethanol led to the formation of 4-(1-chloro-2-ethoxyethyl)pyridine hydrochloride.

It would be desirable to find a simple and clean method of preparing 4-(1-chlorovinyl)pyridine and salts thereof from 4-(1,2-dichloroethyl)pyridine.

SUMMARY OF INVENTION

An object of this invention is to provide a novel process for preparing 4-(1-chlorovinyl)pyridines.

Another object is to provide such a process which results in the formation of the 4-(1-chlorovinyl)pyridine in high yield.

These and other objects are attained by heating an acid salt of 4-(1,2-dichloroethyl)pyridine in an inert solvent until dehydrohalogenation to a 4-(1-chlorovinyl)pyridine is effected.

DETAILED DESCRIPTION

Acid salts utilizable in the practice of the invention are salts of 4-(1,2-dichloroethyl)pyridine with any relatively strong acid, i.e., an acid having a dissociation constant of at least about $1.7 \times 10^{-5}$, preferably at least about $1.0 \times 10^{-1}$, at 25° C. For example, it may be the salt of an inorganic acid, such as sulfuric, hydrochloric, hydrobromic, hydrofluoric, hydroborofluoric, etc., or an organic acid, such as methanesulfonic, acetic, chloroacetic, dichloroacetic, etc. It is preferably a hydrochloride, hydrobromide, or boron trifluoride complex, most preferably a hydrochloric complex.

The inert solvent used in the process may be any solvent that is inert under the conditions of the reaction but is generally an amidic solvent, such as N,N-dimethylformamide, N,N-dimethylacetamide, tetraethyl urea, etc.

The dehydrohalogenation of the invention is accomplished by heating the salt of the 4-(1,2-dichloroethyl)pyridine in the inert solvent at a dehydrohalogenation temperature, e.g., about 50°–150° C., until dehydrohalogenation is effected, generally for at least about 10 minutes. If desired, the dehydrohalogenation may be accomplished in the presence of an agent, such as potassium carbonate, capable of bonding HCl or the like.

The process of the invention results in the formation of 4-(1-chlorovinyl)pyridine or a salt thereof that is easily convertible to the free base by conventional techniques. It is particularly advantageous as a simple, clean method of forming the product, which is useful as a nematocide or as a pharmaceutical precursor—the latter application being more fully described in copending application Ser. No. 532,703, filed Sept. 16, 1983, in the name of V. Ramachandran.

The following examples are given to illustrate the invention and are not intended as a limitation thereof.

EXAMPLE I

A solution of 1 g of 4-(1,2-dichloroethy)pyridine hydrochloride in 10 ml of N,N-dimethylformamide (DMF) was heated to 60° C. for 15 minutes, after which the crude reaction mixture was taken in water and methylene chloride, and excess DMF was removed by washing with methylene chloride. The aqueous layer was made basic to a pH of about 8, and the contents were extracted with four 50 ml aliquots of methylene chloride. The methylene chloride layer was dried, filtered, and evaporated to give 1 g of crude material which analysis determined to contain 95% of 4-(1-chlorovinyl)pyridine, the only inpurity being 4-(1,2-dichloroethyl)pyridine.

EXAMPLE II

A sample of 4-(1,2-dichloroethyl)pyridine/boron trifluoride complex was taken in DMF containing some anhydrous potassium carbonate. The nmr of the solution showed the slow formation of 4-(1-chlorovinyl)pyridine, which accelerated upon heating to 60° C. and subsequently to 100° C. The crude reaction mixture was then taken in methylene chloride and extracted with water to remove DMF. After work-up the nmr showed a fairly clean 4-(1-chlorovinyl)pyridine.

The preceding examples show the effectiveness of the process of the invention in producing 4-(1-chlorovinyl)pyridines. The following examples demonstrate the inferiority of other processes.

COMPARATIVE EXAMPLE A

About 2 g of 4-(1,2-dichloroethyl)pyridine hydrochloride were refluxed in absolute ethanol overnight. Excess ethanol was then evaporated, and the remaining traces were removed on a vacuum pump. The process resulted in the production of 2.5 g of 4-(1-chloro-2-ethoxyethyl)pyridine hydrochloride.

COMPARATIVE EXAMPLE B

An aqueous solution of 3 g of 4-(1,2-dichloroethyl)pyridine hydrochloride in 50 ml of water was heated for three hours over a steam bath, after which the solution was neutralized to a pH of 7–8 with sodium bicarbonate. The organic material was extracted with methylene chloride, and the methylene chloride layer was dried, filtered, and evaporated to give 2.5 g of an oil, only 70% of which was determined to be 4-(1-chlorovinyl)pyridine, with the remainder appearing to be 4-(1-chloro-2-hydroxyethyl)pyridine.

I claim:

1. A process which comprises heating a sulfuric, hydrochloric, hydrobromic, hydrofluoric, hydroborofluoric, methanesulfonic, acetic, chloroacetic, or dichloroacetic salt of 4-(1,2-dichloroethyl)pyridine in an inert solvent selected from N,N-dimethylformamide, N,N-dimethylacetamide, and tetraethylurea to dehydrohalogenate it to a 4-chlorovinyl)pyridine.

2. The process of claim 1 wherein the acid salt is a hydrochloride complex.

3. The process of claim 1 wherein the acid salt is a boron trifluoride complex.

4. The process of claim 1 wherein the solvent is N,N-dimethylformamide.

5. The process of claim 1 wherein the acid salt is heated at a temperature in the range of about 50°–150° C.

* * * * *